United States Patent
Ebertz (10) Patent No.: US 11,434,214 B2
(45) Date of Patent: Sep. 6, 2022

(54) PROCESS FOR THE PREPARATION OF AN ACESULFAME IN A SPRAY REACTOR HAVING A SPECIFIC VELOCITY OF FLOW

(71) Applicant: CHEMADVICE GMBH, Wiesbaden (DE)

(72) Inventor: Hans Wolfgang Ebertz, Troisdorf (DE)

(73) Assignee: CHEMADVICE GMBH, Wiesbaden (DE)

( * ) Notice: Subject to any disclaimer, the term of this patent is extended or adjusted under 35 U.S.C. 154(b) by 67 days.

(21) Appl. No.: 16/954,080

(22) PCT Filed: Dec. 15, 2017

(86) PCT No.: PCT/EP2017/083173
§ 371 (c)(1),
(2) Date: Jun. 15, 2020

(87) PCT Pub. No.: WO2019/114999
PCT Pub. Date: Jun. 20, 2019

(65) Prior Publication Data
US 2020/0331873 A1    Oct. 22, 2020

(51) Int. Cl.
*C07D 291/06* (2006.01)
*B01J 10/00* (2006.01)
*B01J 19/26* (2006.01)

(52) U.S. Cl.
CPC ............ *C07D 291/06* (2013.01); *B01J 10/00* (2013.01); *B01J 19/26* (2013.01)

(58) Field of Classification Search
CPC .......... C07D 291/06; B01J 10/00; B01J 19/26
USPC ............................................. 544/2
See application file for complete search history.

(56) References Cited

U.S. PATENT DOCUMENTS 4,876,341 A * 10/1989 Schutz ................ C07D 291/06
544/2
7,829,701 B2   11/2010 Liu et al.

FOREIGN PATENT DOCUMENTS

| CN | 204320227 U   | 5/2015 |
| CN | 103 613 566 B | 3/2016 |
| DE | 2453063 A1    | 5/1976 |
| DE | 3531357 A1    | 3/1987 |
| WO | 93/19055 B1   | 9/1993 |

OTHER PUBLICATIONS

International Search Report for International Application No. PCT/EP2017/083173 dated Sep. 13, 2018.
Written Opinion for International Application No. PCT/EP2017/083173 dated Sep. 13, 2018.

* cited by examiner

*Primary Examiner* — Kahsay Habte
(74) *Attorney, Agent, or Firm* — Meunier Carlin & Curfman LLC (57) ABSTRACT

In general, the invention relates to a process for the preparation of acesulfame or a derivative thereof. More specifically, the invention relates to a process, to a product obtainable by the process and the use of a specified velocity of flow for improving yield in the preparation of acesulfame or a derivative thereof. The invention relates to a process for the preparation of a product, the product being 6-methyl-3,4-dihydro1,2,3-oxathiazin-4-one 2,2-dioxide or a derivative thereof, the process comprising the following steps: a. Contacting $SO_3$ and acetoacetamide-N-sulfonic acid or a derivative thereof in a reactor with a reactor pressure to obtain the product; b. The product exiting the reactor to a region outside the reactor through an aperture at a velocity of flow higher than 0.9 m/s, the region outside the reactor having an external pressure which is lower than the reactor pressure.

17 Claims, 4 Drawing Sheets

PROCESS FOR THE PREPARATION OF AN ACESULFAME IN A SPRAY REACTOR HAVING A SPECIFIC VELOCITY OF FLOW

CROSS REFERENCE TO RELATED APPLICATION

This is a national stage application of PCT/EP2017/083173 filed Dec. 15, 2017, the contents of which is incorporated herein by reference.

FIELD OF THE INVENTION

In general, the invention relates to a process for the preparation of acesulfame or a derivative thereof. More specifically, the invention relates to a process, to a product obtainable by the process and the use of a specified velocity of flow for improving a process for the preparation of acesulfame or a derivative thereof.

BACKGROUND

Acesulfame and its derivatives are hugely important as sweeteners in food stuffs and in medicines. Of particular interest are the non-toxic salts, of which the potassium salt acesulfame K is most noteworthy. Acesulfame K is often marketed under the tradenames Sunett® and Sweet one and is designated with the E number E950 in the European Union. In view of the huge demand for acesulfame as a sweetener, there is a great need for improved processes for its production and even minor improvements to the production processes can result in huge savings, both economically and ecologically.

Early approaches to acesulfame production employed halogen based intermediates. A number of examples are presented in Angewandte Chemie 85, No. 22 (1973), pages 965 to 73, corresponding to International Edition Vol. 12, No. 11 (1973), pages 869-76. There, the processes overwhelmingly start from chlorosulfonyl or fluorosulfonyl isocyanate. Another example is given in German patent publication number 2,453,063 where a process starting from amidosulfonyl fluoride is disclosed.

A process for the preparation of acesulfame which proceeds via an acetoacetamide-N-sulfonic acid can offer the advantage of starting from more readily accessible starting materials. One example of such a process is presented in Chinese patent application 201310531442. There remains however a need for improved processes for the preparation of acesulfame, in particular in terms of yield and quality of product.

SUMMARY OF THE INVENTION

Generally, it is an object of the present invention to at least partly overcome a disadvantage arising from the prior art.

It is an object of the invention to provide a process for the preparation of acesulfame or a derivative thereof with improved yield.

It is an object of the invention to provide a process for the preparation of acesulfame or a derivative thereof with a reduced requirement for post-treatment.

It is an object of the invention to provide a process for the preparation of acesulfame or a derivative thereof with a reduced proportion of side products.

It is an object of the invention to provide a process for the preparation of acesulfame or a derivative thereof with reduced loss of acesulfame in crystallisation.

It is an object of the invention to provide a process for the preparation of acesulfame or a derivative thereof with reduced environmental impact.

DETAILED DESCRIPTION

Throughout this document, disclosure made in relation to a hydrolysis step is also made in relation to a step of contacting with $H_2O$ and vice versa.

6-methyl-3,4-dihydro1,2,3-oxathiazin-4-one 2,2-dioxide is also called acesulfame and the term acesulfame is used throughout this document as a synonym of 6-methyl-3,4-dihydro1,2,3-oxathiazin-4-one 2,2-dioxide.

A contribution to achieving at least one of the above objects is made by the claims. A contribution to achieving at least one of the above objects is made by the following embodiments, the number of the embodiment being indicated between vertical bars.

|1| A process for the preparation of a product, the product being 6-methyl-3,4-dihydro1,2,3-oxathiazin-4-one 2,2-dioxide or a derivative thereof, the process comprising the following steps:
  a. Contacting $SO_3$ and acetoacetamide-N-sulfonic acid or a derivative thereof in a reactor with a reactor pressure to obtain the product;
  b. The product exiting the reactor to a region outside the reactor through an aperture at a velocity of flow higher than 0.9 m/s, the region outside the reactor having an external pressure which is lower than the reactor pressure.

|2| The process according to embodiment |1|, wherein the velocity of flow is higher than 3 m/s, preferably higher than 4 m/s, more preferably higher than 6 m/s, most preferably higher than 8 m/s. In some cases, the velocity of flow might be as high as about 40 m/s.

|3| The process according to embodiment |1| or |2|, wherein the velocity of flow is in the range from 1 to 20 m/s, preferably in the range from 3 to 17 m/s, more preferably in the range from 5 to 15 m/s.

|4| The process according to any of the preceding embodiments, wherein the reactor has a reactor temperature in the range from −70 to 175° C., preferably in the range from 40 to 150° C., more preferably in the range from 60 to 130° C., most preferably in the range from 80 to 120° C.

|5| The process according to any of the preceding embodiments, wherein the reactor pressure is in the range from 0.2 to 2 MPa, preferably in the range from 0.3 to 1.5 MPa, more preferably in the range from 0.4 to 1.2 MPa, most preferably in the range from 0.5 to 1 MPa.

|6| The process according to any of the preceding embodiments, wherein the external pressure is in the range from 0.01 to 0.5 MPa, preferably in the range from 0.05 to 0.3 MPa, more preferably in the range from 0.07 to 0.2 MPa, most preferably in the range from 0.1 to 0.15 MPa.

|7| The process according to any of the preceding embodiments, wherein the difference between the reactor pressure and the external pressure is in the range from 0.1 to 1.9 MPa, preferably in the range from 0.2 to 1.4 MPa, more preferably in the range from 0.3 to 1.1 MPa, most preferably in the range from 0.5 to 1 MPa.

|8| The process according to any of the preceding embodiments, wherein the aperture has a cross sectional area in the range from 10 $mm^2$ to 500 $mm^2$, preferably in the range from 20 $mm^2$ to 300 $mm^2$, more preferably in the range from 30 mm to 250 $mm^2$, most preferably in the range from 50 mm² to 200 mm². In one aspect of this embodiment, the process is adapted and configured to run with an output of product in the range from 125 to 625 kg/hr.

|9| The process according to any of the preceding embodiments, wherein the aperture is circular.

|10| The process according to any of the preceding embodiments, wherein the product exits the reactor in step b. as a spray.

|11| The process according to any of the preceding embodiments, comprising the following step:
c. The product is contacted with $H_2O$.

|12| The process according to embodiment |11|, wherein step c. is started within 60 seconds of step b., preferably within 30 seconds, more preferably within 15 seconds. The time gap is preferably the time between exit from the reactor and first contact between the product and the $H_2O$. The time gap is preferably determined for a given portion of product, namely as the time gap between the time at which a given portion of product exits the reactor in step b. and the time at which the same given portion of product is contacted with $H_2O$ in step c.

|13| The process according to embodiment |11| or |12|, wherein step c. is started within 0.001 to 60 seconds of step b., preferably 0.01 to 50 seconds, more preferably 0.02 to 40 seconds, most preferably 0.05 to 30 seconds. The time gap is preferably the time between exit from the reactor and first contact between the product and the $H_2O$. The time gap is preferably determined for a given portion of product, namely as the time gap between the time at which a given portion of product exits the reactor in step b. and the time at which the same given portion of product is contacted with $H_2O$ in step c.

|14| The process according to any of the preceding embodiments, wherein the reactor is not actively cooled.

|15| The process according to any of the preceding embodiments, wherein the product is cooled by evaporation of a solvent, preferably evaporation of dichloromethane.

|16| The process according to any of the preceding embodiments, wherein the molar ratio in step a. of the $SO_3$ to the acetoacetamide-N-sulfonic acid or derivative thereof is in the range from 1:1 to 20:1, preferably in the range form 2:1 to 17:1, more preferably in the range from 2.5:1 to 15:1, most preferably in the range from 3:1 to 10:1.

|17| The process according to any of the preceding embodiments, wherein step b. is performed within 10 minutes of step a., preferably within 2 minutes, more preferably within 1 minute. The time gap is preferably the time between the first contact of the reactants in step a. and the time of exit from the reactor. The time gap is preferably determined for a given portion of material, namely as the time gap between the time at which a given portion of material is contacted in step a. and the time at which the same given portion of material exits the reactor in step b.

|18| The process according to any of the preceding embodiments, wherein step b. is performed within 0.001 to 60 seconds of step a., preferably 0.01 to 30 seconds, more preferably 0.02 to 20 seconds, most preferably 0.03 to 10 seconds. The time gap is preferably the time between first contact of the reactants in step a. and the time of exit from the reactor. The time gap is preferably determined for a given portion of material, namely as the time gap between the time at which a given portion of material is contacted in step a. and the time at which the same given portion of material exits the reactor in step b.

|19| The process according to any of the preceding embodiments, wherein the contacting in step a. is performed in the presence of a reaction solvent. In one aspect of this embodiment, the reaction solvent is a chemical compound. In another aspect of this embodiment, the reaction solvent is two or more chemical compounds.

|20| The process according to embodiment |19|, wherein the reaction solvent is an inert solvent. An inert solvent preferably does not react chemically with the acetoacetamide-N-sulfonic acid or derivative thereof. An inert solvent preferably does not react chemically with acesulfame or a derivative thereof. An inert solvent preferably reacts at most minimally with $SO_3$, preferably not consuming more than 1 wt. % of the $SO_3$ in one hour, based on the amount of $SO_3$.

|21| The process according to embodiment |19| or |20|, wherein the reaction solvent comprises a halogenated hydrocarbon. In one aspect of this embodiment, the reaction solvent is a halogenated hydrocarbon.

|22| The process according to any of the embodiments |19| to |21|, wherein the reaction solvent comprises dichloromethane. In one aspect of this embodiment, the reaction solvent is dichloromethane.

|23| The process according to any of the preceding embodiments, wherein the $SO_3$ for the contacting step a. is provided in a first solvent. In one aspect of this embodiment, the first solvent is a chemical compound. In another aspect of this embodiment, the first solvent is two or more chemical compounds.

|24| The process according to embodiment |23|, wherein the first solvent is an inert solvent. An inert solvent preferably does not react chemically with the acetoacetamide-N-sulfonic acid or derivative thereof. An inert solvent preferably does not react chemically with acesulfame or a derivative thereof. An inert solvent preferably reacts at most minimally with $SO_3$, preferably not consuming more than 1 wt. % of the $SO_3$ in one hour, based on the amount of $SO_3$.

|25| The process according to embodiment |23| or |24|, wherein the first solvent comprises a halogenated hydrocarbon. In one aspect of this embodiment, the first solvent is a halogenated hydrocarbon.

|26| The process according to any of the embodiments |23| to |25|, wherein first solvent comprises dichloromethane. In one aspect of this embodiment, the first solvent is dichloromethane.

|27| The process according to any of the embodiments |23| to |26|, wherein the concentration of $SO_3$ in the first solvent is in the range from 0.05 to 20 molar, preferably in the range from 0.1 to 15 molar, more preferably in the range from 0.15 to 10 molar, most preferably in the range from 0.2 to 6 molar.

|28| The process according to any of the preceding embodiments, wherein the acetoacetamide-N-sulfonic acid or a derivative thereof for the contacting step a. is provided in a second solvent. In one aspect of this embodiment, the second solvent is a chemical compound. In another aspect of this embodiment, the second solvent is two or more chemical compounds.

|29| The process according to embodiment |28|, wherein the second solvent is an inert solvent. An inert solvent preferably does not react chemically with the acetoacetamide-N-sulfonic acid or derivative thereof. An inert solvent preferably does not react chemically with acesulfame or a derivative thereof. An inert solvent preferably reacts at most minimally with $SO_3$, preferably not consuming more than 1 wt. % of the $SO_3$ in one hour, based on the amount of $SO_3$.

|30| The process according to embodiment |28| or |29|, wherein the second solvent comprises a halogenated hydrocarbon. In one aspect of this embodiment, the second solvent is a halogenated hydrocarbon.

|31| The process according to any of the embodiments |28| to |30|, wherein second solvent comprises dichloromethane. In one aspect of this embodiment, the second solvent is dichloromethane.

|32| The process according to any of the embodiments |28| to |31|, wherein the concentration of the acetoacetamide-N-sulfonic acid or a derivative thereof in the second solvent is in the range from 0.02 to 5 molar, preferably in the range from 0.03 to 3 molar, more preferably in the range from 0.04 to 2 molar, most preferably in the range from 0.05 to 1.5 molar.

|33| The process according to any of the preceding embodiments, wherein the $SO_3$ for the contacting step a. is provided in a first solvent and the acetoacetamide-N-sulfonic acid or a derivative thereof for the contacting step a. is provided in a second solvent and the first solvent and the second solvent are the same. In one aspect of this embodiment, the first solvent is a chemical compound. In another aspect of this embodiment, the first solvent is two or more chemical compounds.

|34| The process according to embodiment |33|, wherein the first solvent is an inert solvent. An inert solvent preferably does not react chemically with the acetoacetamide-N-sulfonic acid or derivative thereof. An inert solvent preferably does not react chemically with acesulfame or a derivative thereof. An inert solvent preferably reacts at most minimally with $SO_3$, preferably not consuming more than 1 wt. % of the $SO_3$ in one hour, based on the amount of $SO_3$.

|35| The process according to embodiment |33| or |34|, wherein the first solvent comprises a halogenated hydrocarbon. In one aspect of this embodiment, the first solvent is a halogenated hydrocarbon.

|36| The process according to any of the embodiments |33| to |35|, wherein first solvent comprises dichloromethane. In one aspect of this embodiment, the first solvent is dichloromethane.

|37| The process according to any of the preceding embodiments, wherein the product has a purity of higher than 95 wt. %, preferably higher than 99 wt. %, more preferably higher than 99.5 wt. %.

|38| 6-methyl-3,4-dihydro1,2,3-oxathiazin-4-one 2,2-dioxide or a derivative thereof obtainable by a process according to any of the preceding embodiments.

|39| Use of a velocity of flow of a product exiting a reactor of higher than 0.9 m/s for improving yield in the production of 6-methyl-3,4-dihydro1,2,3-oxathiazin-4-one 2,2-dioxide or a derivative thereof.

|40| Use of a velocity of flow of a product exiting a reactor of higher than 0.9 m/s for reducing the requirement for post-treatment in the production of 6-methyl-3,4-dihydro1,2,3-oxathiazin-4-one 2,2-dioxide or a derivative thereof.

|41| Use of a velocity of flow of a product exiting a reactor of higher than 0.9 m/s for reducing the proportion of side-products produced in the production of 6-methyl-3,4-dihydro1,2,3-oxathiazin-4-one 2,2-dioxide or a derivative thereof.

|42| Use of a velocity of flow of a product exiting a reactor of higher than 0.9 m/s for reducing the proportional loss of product in crystallisation in the production of 6-methyl-3,4-dihydro1,2,3-oxathiazin-4-one 2,2-dioxide or a derivative thereof.

|43| Use of a velocity of flow of a product exiting a reactor of higher than 0.9 m/s for reducing environmental impact in the production of 6-methyl-3,4-dihydro1,2,3-oxathiazin-4-one 2,2-dioxide or a derivative thereof.

Process

A contribution to achieving at least one of the above mentioned objects is made by a process for the preparation of a product, the product being 6-methyl-3,4-dihydro1,2,3-oxathiazin-4-one 2,2-dioxide or a derivative thereof, the process comprising the following steps:
   a. Contacting $SO_3$ and acetoacetamide-N-sulfonic acid or a derivative thereof in a reactor with a reactor pressure to obtain the product;
   b. The product exiting the reactor to a region outside the reactor through an aperture at a velocity of flow of higher than 0.9 m/s, the region outside the reactor having an external pressure which is lower than the reactor pressure.

A contribution is made by a process further comprising one or both of the following steps:
   c. Contacting with $H_2O$.
   d. Further steps, such as separation, extraction and purification.

In one embodiment, the process may comprise a series of chemical reactions as presented in the following chemical equation I:

In other embodiments, the process may comprise a series of chemical reactions similar to those presented in chemical equation I. In one aspect of this embodiment, the diketene adduct has a cation different to $HNEt_3^+$ (triethyl ammonium), preferably one or more selected from the group consisting of $Na^+$, $K^+$, $Ca^+$, $Li^+$, ammonium and an aliphatic ammonium other than $HNET_3^+$. In one aspect of this embodiment, a solvent other than $CH_2Cl_2$ is employed, preferably one selected from the solvents section below. In one aspect of this embodiment, a base different to KOH is employed and the resulting acesulfame has a correspondingly different cation. In one aspect of this embodiment, an equimolar amount of $SO_3$ is employed, namely the parameter n is set to 1. Here, the formula (n−1) is equal to zero and no $H_2O$ is employed.

The process of the invention preferably includes a ring closure reaction in which the acetoacetamide-N-sulfonic acid or derivative thereof reacts to form a ring. The ring closure is preferably assisted by the $SO_3$.

In one embodiment of the process, a step of contacting with $H_2O$ c. is performed subsequently to step b. A step of contacting with $H_2O$ is preferably employed for hydrolysing an adduct, preferably an adduct comprising $SO_3$.

In one embodiment of the process, further steps are included. Preferred steps are separation, extraction and purification and preferably are performed after the exit step b., preferably after a step of contacting with $H_2O$ c. Separation preferably precedes extraction. Separation preferably precedes purification. Purification is preferably performed after separation. Purification is preferably performed after extraction. Examples of further steps are distillation, crystallisation, deposition on a surface, centrifuging, filtration, acid treatment and alkaline treatment.

In a preferred embodiment, the process comprises a spraying. The spraying preferably occurs as the product exits the reactor, preferably via a circular aperture. A preferred aperture is adapted and configured to result in a pressure drop between the reactor and outside the reactor, preferably a pressure drop of more than 0.5 bar. A preferred aperture is adapted and configured to cause spraying of the product.

Hydrolysis

A contribution to achieving at least one of the above described objects is made by a process comprising a hydrolysis step. A hydrolysis step is preferably a step of contacting the product with $H_2O$. Throughout this document, disclosure made in relation to a hydrolysis step is also made in relation to a step of contacting with $H_2O$ and vice versa. A hydrolysis step is particularly preferred where the product is an adduct, preferably an adduct with $SO_3$. Where a hydrolysis is performed, a separation step is preferably also performed for removing a hydrolysis product, preferably for removing sulphuric acid.

In one embodiment, the step of contacting with $H_2O$ is performed in the same apparatus as the contacting step a.

It is preferred for the step of contacting with $H_2O$ to be performed soon after step b. in which the product exits the reactor. In one embodiment, the product exits the reactor in form of a spray due to evaporation of solvent and is contacted with $H_2O$ in a mixing apparatus in which the product is brought continuously in contact with $H_2O$. In one embodiment, the apparatus for contacting with $H_2O$ is a stirred vessel.

The step of contacting with $H_2O$ preferably produces a mixture comprising acesulfame or a derivative thereof, sulphuric acid and $H_2O$. The amount of $H_2O$ employed in the step of contacting with $H_2O$ is preferably selected such that the resulting mixture comprises a weight ratio of sulphuric acid:$H_2O$ in the range from 1:10 to 10:1, preferably in the range from 1:3 to 5:1, more preferably in the range from 1:1 to 3:1. In one embodiment, the step of contacting with $H_2O$ is performed as a continuous process. In this embodiment, the ratio of sulphuric acid to $H_2O$ is set by adapting a flow rate of $H_2O$.

In one embodiment, the $H_2O$ for the contacting step c. is in a vapour phase. In one embodiment, the $H_2O$ for the contacting step c. is in a liquid phase. In one embodiment, the $H_2O$ for the contacting step c. comprises a vapour phase and a liquid phase.

Reactor

The contacting step a. is carried out in a reactor. The reactor is preferably configured and adapted to withstand elevated pressure and elevated temperature. In one embodiment, the reactor is configured and adapted to withstand the temperatures employed for the contacting step a. In another embodiment, the reactor is configured and adapted to withstand temperatures up to 140° C., preferably 175° C., more preferably up to 200° C. In one embodiment, the reactor is configured and adapted to withstand the pressures employed for the contacting step a. In another embodiment, the reactor is configured and adapted to withstand pressures up to 1.6 MPa, preferably up to 2.5 MPa, more preferably up to 3.2 MPa.

In one embodiment, the reactor is a tubular reactor, preferably a cylindrical tubular reactor. In one embodiment, the reactor comprises a tube, preferably a cylindrical tube. The interior of a tube or of a tubular reactor is also referred to as a bore. The tube is preferably adapted and configured to result in a pressure drop between the reactor and outside the reactor, preferably a pressure drop of more than 0.5 bar. A preferred tube is adapted and configured to cause spraying of the product.

The reactor preferably contains a mixer, preferably a static mixer.

Aperture

The product exits the reactor through an aperture. In one embodiment, the aperture is circular.

In one embodiment, the aperture is an exit from a tube, also known as a pipe.

In one embodiment, the reactor comprises a tube and the aperture is an exit from the tube, preferably an open end of the tube. In one aspect of this embodiment, the tube is cylindrical and the aperture is circular. In one aspect of this embodiment, the tube of the reactor may have a larger cross-sectional diameter than the aperture. The tube preferably contains a static mixer and the cross sectional diameter of the tube is preferably determined at the static mixer.

A preferred aperture is adapted and configured to result in a pressure drop between the reactor and outside the reactor, preferably a pressure drop of more than 0.5 bar.

$SO_3$

A contribution to achieving at least one of the above mentioned objects is made by a process in which $SO_3$ is employed as a starting material. $SO_3$ is preferably employed in an amount by mols which is at least equal to the amount by mols of the acetoacetamide-N-sulfonic acid or a derivative thereof, preferably with the molar ratio in step a. of the $SO_3$ to the acetoacetamide-N-sulfonic acid or derivative thereof being in the range from 1:1 to 20:1, preferably in the range form 2:1 to 17:1, more preferably in the range from 2.5:1 to 15:1, most preferably in the range from 3:1 to 10:1. In one embodiment, $SO_3$ is employed in an approximately equimolar 30 amount to the acetoacetamide-N-sulfonic acid or a derivative thereof. In this case, it can be that insufficient $SO_3$ is present for forming an adduct. In one aspect of this embodiment no step of contacting with $H_2O$ is required. In one embodiment, a molar excess of $SO_3$ is employed, preferably with the molar ratio in step a. of the $SO_3$ to the acetoacetamide-N-sulfonic acid or derivative thereof being in the range from greater than 1:1 to 20:1, preferably in the range form 2:1 to 17:1, more preferably in the range from 2.5:1 to 15:1, most preferably in the range from 3:1 to 10:1.

In one embodiment of the invention, $SO_3$ is provided in step a. in a first solvent.

In another embodiment, $SO_3$ is provided in step a. as a liquid.

Acetoacetamide-N-Sulfonic Acid or a Derivative Thereof

Acetoacetamide-N-sulfonic acid or a derivative thereof is employed in the process according to the invention. Acetoacetamide-N-sulfonic acid is also known by its chemical formula $CH_3COCH_2CONHSO_3H$ and the term Acetoacetamide-N-sulfonic acid and the formula $CH_3COCH_2CONHSO_3H$ shall be used interchangeably in this document.

Preferred derivatives of Acetoacetamide-N-sulfonic acid are salts, preferably having the formula $CH_3COCH_2CONHSO_3^-M^+$. A preferred $M^+$ is selected from the group consisting of $Na^+$, $K^+$ $Ca^+$, $Li^+$, ammonium and an aliphatic ammonium. Preferred aliphatic ammoniums in this context are one or more selected from the group consisting of: monoethyl ammonium, diethyl ammonium, triethyl ammonium, methyl ammonium, dimethyl ammonium and tri methyl ammonium. The preferred aliphatic ammonium is triethyl ammonium.

The Acetoacetamide-N-sulfonic acid or derivative thereof might be procured or formed in a process preceding step a. of the process of the invention. On preferred route for forming Acetoacetamide-N-sulfonic acid or a derivative thereof is by reacting amidosulfonic acid or a derivative thereof with an acetoacetylating agent, preferably in approximately equimolar 30 amounts. Preferred derivatives of amidosulfonic acid in this contexts are salts, preferably with a cation selected form the group consisting of $Na^+$, $K^+$, $Ca^+$, $Li^+$, ammonium and an aliphatic ammonium. Preferred aliphatic ammoniums in this context are one or more selected from the group consisting of: monoethyl ammonium, diethyl ammonium, triethyl ammonium, methyl ammonium, dimethyl ammonium and tri methyl ammonium. The preferred aliphatic ammonium is triethyl ammonium.

The preferred acetoacetylating agent is diketene.

In one embodiment, the acetoacetamide-N-sulfonic acid or derivative thereof for the contacting step a. is provided in a second solvent.

Solvents

One or more solvents may be employed in the process of the invention, for example in one or more of the following roles: as a vehicle for the $SO_3$, as a vehicle for the acetoacetamide-N-sulfonic acid or derivative thereof, as a reaction medium in the reactor or for providing evaporative cooling.

Preferred solvents for the acetoacetamide-N-sulfonic acid or derivative thereof are inert solvents. An inert solvent preferably does not react chemically with the acetoacetamide-N-sulfonic acid or derivative thereof. An inert solvent preferably does not react chemically with acesulfame or a derivative thereof. An inert solvent preferably reacts at most minimally with $SO_3$, preferably not consuming more than 1 wt. % of the $SO_3$ in one hour, based on the amount of $SO_3$. Preferred solvents for the acetoacetamide-N-sulfonic acid or derivative thereof are one or more selected from the group consisting of the following: halogenated aliphatic hydrocarbons, aliphatic sulfoxides and aliphatic sulfones. Preferred halogenated aliphatic hydrocarbons have up to four carbon atoms, preferably one or more selected from the group consisting of the following: methylene chloride, chloroform and 1,2-dichloroethane. The preferred aliphatic sulfoxide is dimethyl sulfoxide. The preferred aliphatic sulfone is sulfolane. In one embodiment, the solvent for the acetoacetamide-N-sulfonic acid or derivative thereof is one or more selected form the group consisting of the following: methylene chloride and 1,2-dichloroethane, preferably methylene chloride.

Preferred solvents for the $SO_3$ are inert solvents. An inert solvent preferably does not react chemically with the acetoacetamide-N-sulfonic acid or derivative thereof. An inert solvent preferably does not react chemically with acesulfame or a derivative thereof. An inert solvent preferably reacts at most minimally with $SO_3$, preferably not consuming more than 1 wt. % of the $SO_3$ in one hour, based on the amount of $SO_3$. Preferred solvents for the $SO_3$ may be inorganic solvents or organic solvents or both. The preferred inorganic solvent is $SO_2$. Preferred organic solvents are one or more selected from the group consisting of the following: halogenated aliphatic hydrocarbons, aliphatic sulfones. Preferred halogenated aliphatic hydrocarbons have up to four carbon atoms, preferably one or more selected form the group consisting of the following: methylene chloride, chloroform and 1,2-dichloroethane. The preferred aliphatic sulfone is sulfolane. In one embodiment, the solvent is $SO_2$ or methylene chloride or both.

In a preferred embodiment of the process according to the invention the same solvent is used both for the acetoacetamide-N-sulfonic acid or derivative thereof and for the $SO_3$. Preferred solvents in this context are halogenated aliphatic hydrocarbons, most preferably methylene chloride.

Cooling

Heat is generally liberated in the reactor by exothermic reaction. The reactor and/or the product can be cooled either by active cooling or passive cooling. Examples of active cooling are one or more of the following: a cooling jacket and immersed cooling pipes. One example of the use of active cooling is given in U.S. Pat. No. 7,829,701 B2. Examples of passive cooling are one or more of the following: conductive fins and gas expansion. In one embodiment, cooling is provided by evaporation of solvent. Evaporation of solvent preferably occurs at the external pressure, which is lower than the reactor pressure. In one aspect of this embodiment, no active cooling is performed. In one embodiment, cooling is provided by evaporation of dichloromethane. Evaporation of dichloromethane preferably occurs at the external pressure, which is lower than the reactor pressure. Preferably the evaporated dichloromethane is condensed and reused in earlier steps. In one aspect of this embodiment, no active cooling of the reaction product is performed.

Product

The process of the invention is preferably for the preparation of 6-methyl-3,4-dihydro1,2,3-oxathiazin-4-one 2,2-dioxide or a derivative thereof. 6-methyl-3,4-dihydro1,2,3-oxathiazin-4-one 2,2-dioxide is also called acesulfame and the term acesulfame is used throughout this document as a synonym of 6-methyl-3,4-dihydro1,2,3-oxathiazin-4-one 2,2-dioxide.

The product of the present invention can be used as a food ingredient, preferably as a sweetener. Quite often, acesulfames are categorised as high intensity sweeteners. In one embodiment, the acesulfame or derivative thereof is non-toxic. In one embodiment, the acesulfame or derivative thereof can be hydrolysed, preferably at elevated temperature in acidic media, preferably resulting in non-toxic hydrolysis products.

Acesulfame is often prepared or usefully employed in the form of a salt. In one embodiment, the product is a salt of acesulfame. Preferred salts of acesulfame comprise the conjugate base of acesulfame and a cation. Preferred cations in this context are one or more selected from the group consisting of the following: $Na^+$, $K^+$, $Ca^+$ and aspartame, preferably $K^+$. In one embodiment, the preferred cation is selected form the group consisting of $Na^+$, $K^+$ and $Ca^+$, preferably $K^+$. In another embodiment, the cation is aspartame. The salt is preferably formed by removing the acidic hydrogen from the nitrogen atom of the acesulfame or derivative thereof. The product of the present invention can be used as a food ingredient. In one embodiment, the acesulfame salt is non-toxic. In one embodiment, the acesulfame salt can be hydrolysed, preferably at elevated temperature in acidic media, preferably resulting in non-toxic hydrolysis products.

Acesulfame can be prepared in the form of an adduct, either as an end product or as an intermediate. In one embodiment, the product is an adduct comprising acesulfame or a derivative thereof. Preferred adducts are formed with electron acceptors, also called Lewis acids. In one aspect of this embodiment, the preferred adduct is formed with $SO_3$. In one aspect of this embodiment, the product is an adduct of 6-methyl-3,4-dihydro1,2,3-oxathiazin-4-one 2,2-dioxide with $SO_3$ also called acesulfame:$SO_3$ adduct. The acesulfame:$SO_3$ adduct may comprise 1 or more $SO_3$ entities. In one aspect the acesulfame:$SO_3$ adduct may comprise 1, 2, 3, 4, 5, 6, 7 or 8 $SO_3$ entities. In one aspect the acesulfame:$SO_3$ adduct may comprise 1 to 8 $SO_3$ entities, preferably 1 to 7, more preferably 1 to 6, more preferably still 1 to 5. The product of the present invention can be used as a food ingredient. In one embodiment, the adduct is non-toxic. In one embodiment, the adduct can be hydrolysed to obtain non-toxic hydrolysis products.

The product may be a mixture, preferably having one or more constituents selected from the group consisting of: acesulfame, an acesulfame adduct and any other derivative of acesulfame. In one embodiment, the product comprises compounds with differing degrees of adduction. In one aspect of this embodiment, the product comprises acesulfame and one or more acesulfame adducts, the adducts preferably being with $SO_3$.

Test Methods

The following test methods are used for features disclosed in this document. In the absence of a test method, the ISO test method for the feature to be measured published most recently before the earliest filing date of the present application applies. In the absence of measuring conditions, a temperature of 298.15 K (25° C., 77° F.) and an absolute pressure of 100 kPa (14.504 psi, 0.986 atm) apply.

Detection of Chemical Species and Concentrations

Acesulfame content is determined by a combination of HPLC and UV spectroscopy according to the procedure described in "Monograph D acesulfame-K USP-NF" as published by "The United States Pharmacopeia and The National Formulary". The version of the monograph published most recently before the earliest filing or priority date of this document is employed.

Acetoacetamide-N-sulfonic acid salt content is calculated based on the contents of the input streams to the process.

$SO_3$ content is determined by distillation.

The content of solvents is determined by gas chromatography and Karl Fisher titration.

The yield of acesulfame is calculated based on the input content of sulfamic acid.

Reactor Temperature

The temperature in the reactor is calculated based on the reactor pressure according to the Antoine equation as follows:

$$\log_{10} p = A - B/(C+T)$$

in which p is the reactor pressure in bar (105 Pa), T is the reactor temperature in K and the three constants have the following values:

A=3.97323, B=1016.865, C=−56.623

Reactor Pressure & External Pressure

Pressure is measure using a piezo-resistive pressure transmitter Rosemount™ 3051 Coplanar™

Velocity of Flow Out of Reactor

The velocity of flow out of the reactor is determined based on the flow rate of input materials, which are measured using the EMERSON Micro Motion™ R-Series apparatus.

Cross Sectional Area of the Aperture

The cross sectional area and diameter of the aperture are measured with a calliper.

Times and Durations

The time gap between the contacting in step a. and exit from the reactor in step b. is calculated based on the input flow rates as measured using the EMERSON Micro Motion™ R-Series apparatus.

The time gap between exit from the reactor in step b. and contacting with $H_2O$ in step c. is calculated based on the velocity of flow of the product out of the reactor

SUMMARY OF THE FIGURES

The invention is now further elucidated with reference to the figures. The figures and figure descriptions are exemplary and are not to be considered as limiting the scope of the invention.

DESCRIPTION OF THE FIGURES

Figure 1:
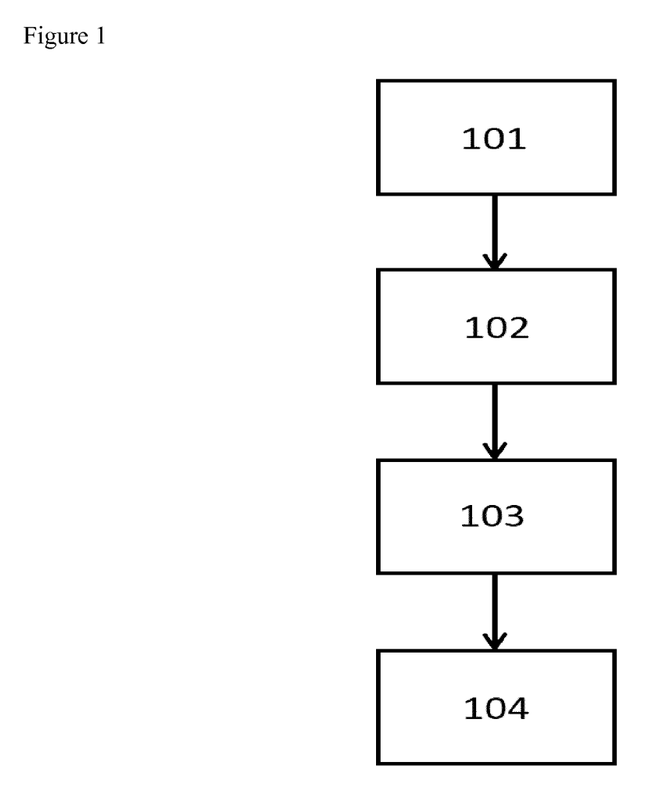
FIG. 1 is a flow diagram showing a process according to the invention.

FIG. 1 is a flow diagram showing a process according to the invention. In step a. 101 an acetoacetamide-N-sulfonic acid or derivative thereof is contacted with $SO_3$ in a reactor. In this case the triethyl ammonium salt of acetoacetamide-N-sulfonic acid dissolved in dichloromethane is contacted with $SO_3$, also dissolved in dichloromethane. In this case the temperature in the reactor is 105° C. and the pressure in the reactor is 0.7 MPa. In step b. 102, the product sprays out of the reactor through an aperture having a cross sectional area of 110 mm to outside of the reactor where the pressure is atmospheric. The velocity of flow through the aperture is 10 m/s. On exiting the reactor and reducing in pressure, some of the dichloromethane solvent evaporates and the temperature of the product reduces to 40° C. In this case, an optional hydrolysis step c. 103 is performed. The product which has sprayed out of the reactor falls onto a hydrolysis bed which is provided with a flow of $H_2O$, thereby hydrolysing and liberating sulphuric acid. In this case several optional further steps 104 are performed to separate the dichloromethane, acesulfame product, $H_2O$ and sulphuric acid.

Figure 2:
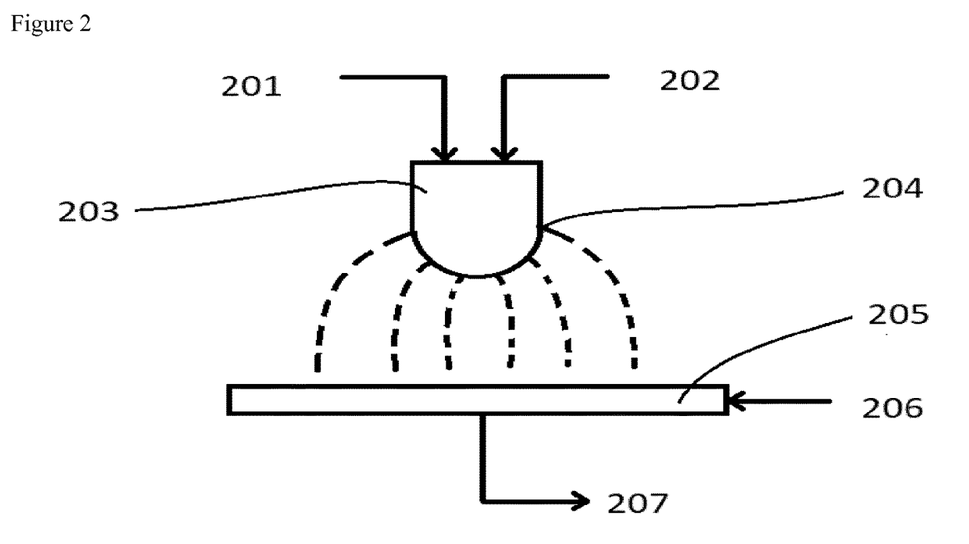
FIG. 2 is a schematic diagram showing a reactor and hydrolysis bed.

FIG. 2 is a schematic diagram showing a reactor 203 and hydrolysis bed 205. An acetoacetamide-N-sulfonic acid derivative supply 201, in this case the triethylammonium salt of acetoacetamide-N-sulfonic acid dissolved in dichloromethane, and an SO₃ supply 202, in this case SO₃ dissolved in dichloromethane, are provided to the reactor 203 and react there to an acesulfame product, in this case an adduct of acesulfame with SO₃. The product exits from the reactor 203 from the apertures 204 as a spray and descends onto a hydrolysis bed 205 having an H₂O supply 206 where it is hydrolysed. The hydrolysis products 207 are removed from the hydrolysis bed and optionally passed to further processes, for example for separating solvents, products and by-products.

Figure 3:
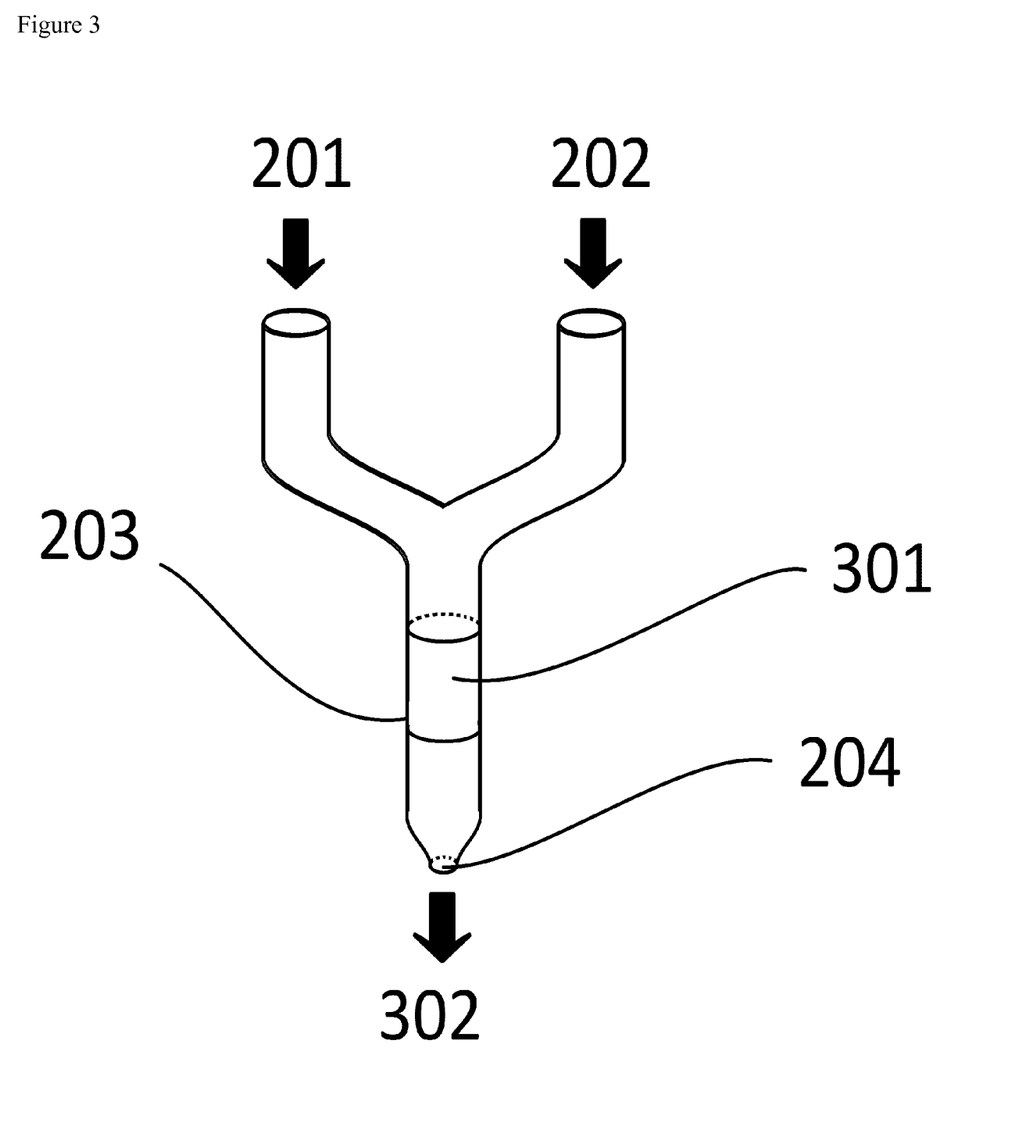
FIG. 3 shows a schematic diagram of a tubular reactor.

FIG. 3 shows a schematic diagram of a tubular reactor. An acetoacetamide-N-sulfonic acid supply 201 and an SO₃ supply 202 enter the reactor 203, each via a tube. The reactor 203 is itself a cylindrical tube. The supplies 201 & 202 in this case are mixed by a static mixer 301. The static mixer 301 has the same cross-sectional diameter as the reactor 203. The product 302 leaves the reactor 203 via a circular aperture 204. In this case, the diameter of the aperture 204 is less than the cross-sectional diameter of the reactor 203. The cross-sectional diameter of the reactor 203 is determined at the static mixer 301. On exiting the reactor 203 via the aperture 204, the product 302 turns into a spray due to evaporation of solvent.

Figure 4:
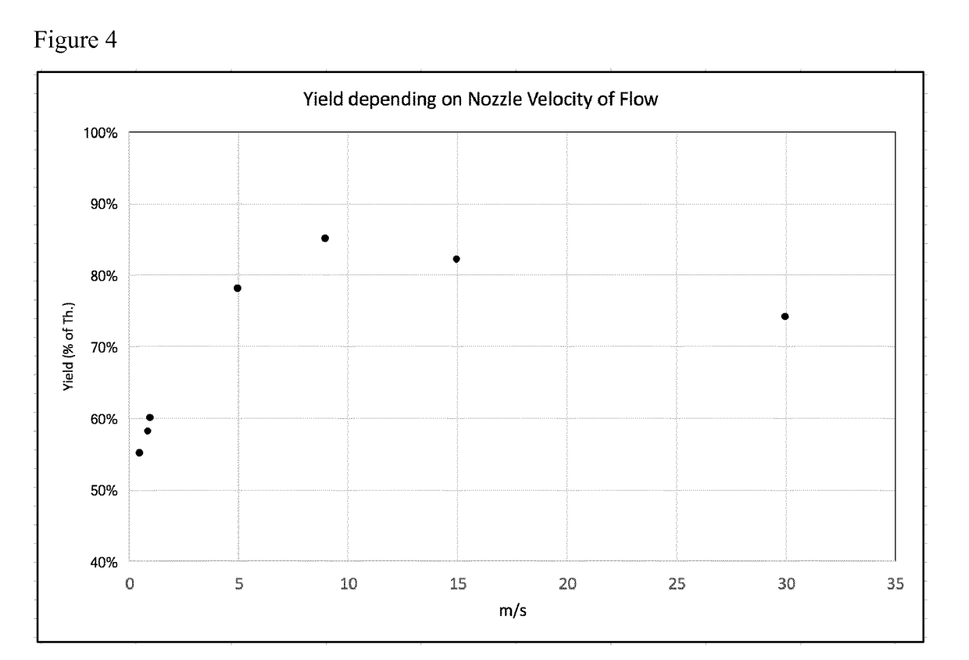
FIG. 4 shows a plot of yield against velocity of flow.

FIG. 4 shows a plot of yield against velocity of flow for the process of the invention. Yield is expressed as a proportion of the theoretical maximum yield.

Figure 5:
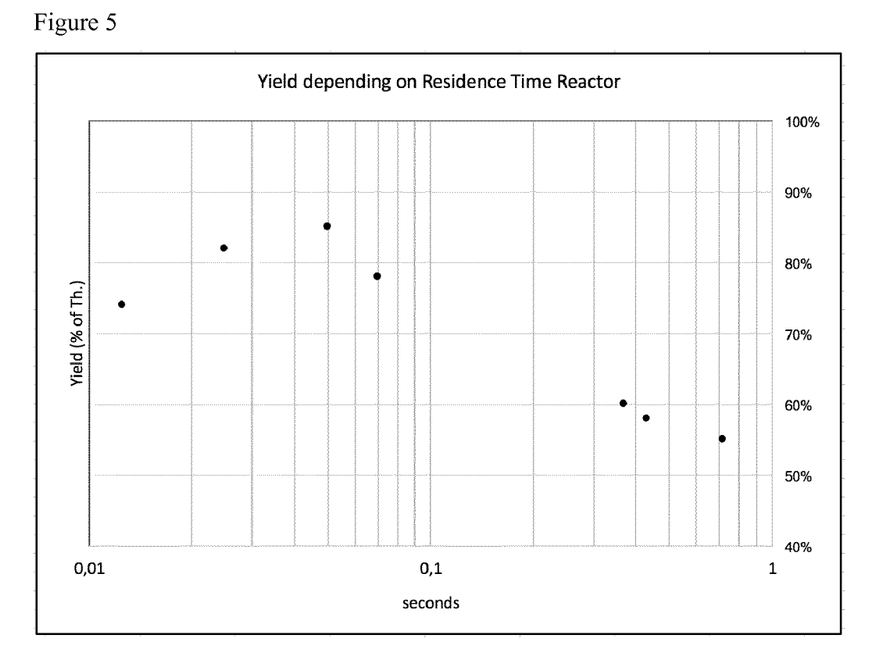
FIG. 5 shows a plot of yield against reaction time.

FIG. 5 shows a plot of yield against reaction time for the process of the invention. Yield is expressed as a proportion of the theoretical maximum yield.

REFERENCE LIST

101 Contacting Step a.
102 Exiting Step b.
103 Optional hydrolysis step c.
104 Optional further steps
201 acetoacetamide-N-sulfonic acid supply
202 SO₃ supply
203 Reactor
204 Aperture
205 Hydrolysis bed
206 Water supply
207 Hydrolysis products
301 Mixer
302 Product

EXAMPLES

The invention is now further elucidated with the aid of examples. These examples are for illustrative purposes and are not to be considered as limiting the scope of the invention.

Examples 1 to 6

A device was provided according to FIG. 2. The acetoacetamide-N-sulfonic acid supply was the triethylammonium salt of Acetoacetamide-N-sulfonic acid dissolved in dichloromethane (DKA) at a concentration of 1.5 molar. The SO₃ supply was SO₃ dissolved in dichloromethane (DCM/SO₃) at a concentration of 5 molar. The two supplies were provided to the reactor with volume flow ratio DKA:DCM/SO₃ of 1:1.2 and the total flow rate was dynamically adjusted such that the product ejected from the reactors with a velocity of flow as given for the particular example in table 1. The supply of H₂O to the hydrolysis bed was adjusted such that the ratio of sulphuric acid:H₂O by weight in the hydrolysis products was 3:1.

TABLE 1

Yield of acesulfame depending on velocity of flow and reaction time

| Example # | Velocity of flow through aperture [m/s] | Yield (% of theoretical maximum) | Reaction Time [s] | Consumption compared with optimum run as reference |
|---|---|---|---|---|
| 1 | 0.5 | 55% | 0.72 | +55% |
| 2 | 0.9 | 58% | 0.43 | +47% |
| 3 | 1 | 60% | 0.37 | +42% |
| 4 | 5 | 78% | 0.07 | +9% |
| 5 | 9 | 85% | 0.05 | REF |
| 6 | 15 | 82% | 0.025 | +4% |
| 7 | 30 | 74% | 0.013 | +15% |

The consumption parameter is calculated as the total cash cost of raw materials, energy consumption, the cost of working up of solvents and auxiliary materials, waste generation with its respective incineration cost as well as the treatment of effluents and off-gas. The consumption parameter is determined by producing a fixed mass of acesulfame K product. The consumption parameter thus represents both the economical and the ecological efficiency of the process.

FIG. 4 shows the yield of the reaction as a proportion of the theoretical maximum yield plotted graphically against the velocity of flow. FIG. 5 shows the yield of the reaction as a proportion of the theoretical maximum yield plotted graphically against the reaction time.

The invention claimed is:

1. A process for the preparation of a product, the product being 6-methyl-3,4-dihydro1,2,3-oxathiazin-4-one 2,2-dioxide or a derivative thereof, the process comprising the following steps:
    a. contacting SO₃ and acetoacetamide-N-sulfonic acid or a derivative thereof in a reactor with a reactor pressure to obtain the product;
    b. the product exiting the reactor to a region outside the reactor through an aperture at a velocity of flow in the range from 3 to 17 m/s, the region outside the reactor having an external pressure which is lower than the reactor pressure.

2. The process according to claim 1, wherein the velocity of flow is in the range from 5 to 15 m/s.

3. The process according to claim 1, wherein the reactor has a reactor temperature in the range from −70 to 175° C.

4. The process according to claim 1, wherein the reactor pressure is in the range from 0.2 to 2 MPa.

5. The process according to claim 1, wherein the external pressure is in the range from 0.01 to 0.5 MPa.

6. The process according to claim 1, wherein the difference between the reactor pressure and the external pressure is in the range from 0.1 to 1.9 MPa.

7. The process according to claim 1, wherein the aperture has a cross sectional area in the range from 10 mm² to 500 mm².

8. The process according to claim 1, wherein the product exits the reactor in step b. as a spray.

9. The process according to claim 1, comprising the following step:
    c. the product is contacted with H₂O.

10. The process according to claim 9, wherein step c. is started within 60 seconds of step b.

11. The process according to claim 1, wherein the product is cooled by evaporation of a solvent.

12. The process according to claim 1, wherein the molar ratio in step a. of the $SO_3$ to the acetoacetamide-N-sulfonic acid or derivative thereof is in the range from 1:1 to 20:1.

13. The process according to claim 1, wherein step b. is performed within 10 minutes of step a.

14. The process according to claim 1, wherein the contacting in step a. is performed in the presence of a reaction solvent, wherein the reaction solvent comprises dichloromethane.

15. The process according to claim 1, wherein the $SO_3$ for the contacting step a. is provided in a first solvent, wherein the first solvent comprises dichloromethane.

16. The process according to claim 1, wherein the acetoacetamide-N-sulfonic acid or a derivative thereof for the contacting step a. is provided in a second solvent, wherein the second solvent comprises dichloromethane.

17. The process according to claim 1, wherein the $SO_3$ for the contacting step a. is provided in a first solvent and the acetoacetamide-N-sulfonic acid or a derivative thereof for the contacting step a. is provided in a second solvent and the first solvent and the second solvent are the same.

\* \* \* \* \*